US00PP18172P2

(12) United States Plant Patent
Gossett

(10) Patent No.: US PP18,172 P2
(45) Date of Patent: Oct. 30, 2007

(54) ***PENSTEMON* PLANT NAMED 'PARTY DRESS'**

(50) Latin Name: ***Penstemon* spp.**
Varietal Denomination: Party Dress

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 5 days.

(21) Appl. No.: 11/452,684

(22) Filed: Jun. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Klarquist Sparkman, LLP

(57) ABSTRACT

A new and distinct *Penstemon* plant characterized by lavender pink flowers which rebloom.

1 Drawing Sheet

Botanical denomination: *Penstemon* spp.
Variety designation: 'Party Dress'.

BACKGROUND OF THE INVENTION

The present invention relates to a new and distinct cultivar of a suffrutescent perennial, *Penstemon* hybrid, and given the cultivar name 'Party Dress'. *Penstemon* is of the family Scrophulariaceae. This new cultivar originated as a seedling selection from a cultivated area from selected generations of Saskatoon Hybrids. The Saskatoon Hybrids are a hybrid seed strain involving *Penstemon barbatus, P. glaber, P. clutei, P. palmeri,* and others.

SUMMARY OF THE INVENTION

This new cultivar is characterized by:

1) Lavender pink flowers.
2) Persistent basal foliage with a compact habit.
3) Reblooming.
4) More tolerant to winter wet soil conditions than most *Penstemon* species or varieties.

This new cultivar has been reproduced only by asexual propagation (division and tissue culture). Each of the progeny exhibits identical characteristics to the original plant. Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a one-year-old *Penstemon* 'Party Dress' growing in the ground in the trial field in full sun in Canby, Oreg.

DETAILED PLANT DESCRIPTION

The following is a detailed description of the new *Penstemon* hybrid based on observations of one-year-old specimens grown in the ground in the trial field in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart.

Plant:
- *Type.*—Suffrutescent, herbaceous perennial.
- *Form.*—Compact basal rosette with mostly upright flowering stems.
- *Hardiness.*—USDA Zone 4 to 9.
- *Size.*—15 cm tall and 33 cm wide without flowering stems, 29 cm tall with flowers.
- *Vigor.*—Excellent.
- *Roots.*—Fibrous, freely branching, fine, and white in color, roots develop slowly from stem cuttings.

Stem leaves:
- *Type.*—Simple.
- *Arrangement.*—Opposite on internodes growing to 6 cm.
- *Shape.*—Lanceolate.
- *Venation.*—Pinnate.
- *Margins.*—Entire.
- *Apex.*—Acuminate.
- *Base.*—Sessile, obtuse.
- *Blade size.*—Grows to 14.5 cm long and 2.2 cm wide.
- *Surface texture.*—Glabrous, shiny.
- *Leaf color.*—Deep green, between Yellow Green 147A and Green 137A top and bottom, with prominent main vein on bottom, Yellow Green 145C.

Basal leaves: Same as above except internodes only grow to 1.5 cm and leaves only grow to 5.5 cm long and 1.5 cm wide, petiolate, petioles grow to 2.5 cm long, Yellow Green 145C.

Inflorescence:
- *Type.*—Thyrse, virgate and weakly secund.
- *Number of flowers.*—30 to 40 per raceme.

*Peduncle.*—Sometimes decumbent, grows to 29 cm tall and 6 mm wide, between Yellow Green 145C and Yellow Green 152C, glabrous (see Stem leaves above for leaves).

*Pedicel.*—Grows to 1 cm long, glabrous, Yellow Green 144A.

*Bloom period.*—June to August.

Flower bud:

*Size.*—2.2 cm long and 9 mm wide.

*Description.*—Closed tubular, bulging at the end.

*Color.*—Red Purple 70C on top and Purple 75B on the bottom with narrow purple lines Violet Blue 90C.

Flower:

*Type.*—Perfect, zygomorphic.

*Shape.*—Tubular, bilabiate, with a narrow tube for 8 mm, inflating for 15 mm, flaring into the lobes; two top lobes shallowly cut and three bottom more deeply divided, flare down, and curl back at the sides.

*Size.*—Grows to 3 cm long and 1.7 cm wide at flare.

*Color.*—Tube outside is Red Purple 70C lightening to Red Purple 70D, inner lobes Purple 75B, tube Purple 75D with lines of Purple 77A as bee tracks to the base.

*Calyx.*—Campanulate with 5 lobes, cut ¾ to base, overlapping, ovate shaped lobes, margins irregularly serrate, acuminate tip 4 mm deep and 35 mm wide, Green 137B.

*Stamen description.*—5, one sterile without an anther, held within the corolla, filaments 8 mm long, White 155A, anthers held parallel to the filaments, dehiscent across the connective, bearded on backsides, 4 mm long, Purple 70A on top side and Purple 75A on bottom side, pollen White 155D.

*Pistil.*—18.5 mm long, ovary 3 mm long and Yellow Green 146C, style 15 mm, Purple 75C.

*Fragrance.*—None.

*Lastingness.*—Each raceme blooms for about 3 weeks on the plant. Removal of spent cymes will induce secondary and tertiary bloom periods. This greatly extends the bloom period.

Fruit:

*Type.*—Capsule.

*Fertility.*—Good.

*Size.*—1 cm deep and 0.4 cm wide.

*Color.*—Greyed Orange 65A.

Seed:

*Shape.*—Irregular.

*Size.*—2 mm. long.

*Color.*—Brown 200A.

Disease and pest resistance: Excellent disease tolerance to root rot, a common problem for *Penstemon.* Leaf spot, rust, and powdery mildew may be a problem, but have not been observed on *Penstemon* 'Party Dress'.

Comparisons to similar *Penstemon:* Compared to *Penstemon* 'Pink Chablis' (U.S. Plant Pat. No. 13,422), *Penstemon* 'Party Dress' has soft lavender pink flowers rather than deep coral pink.

I claim:

1. A new and distinct *Penstemon* plant substantially as shown and described.

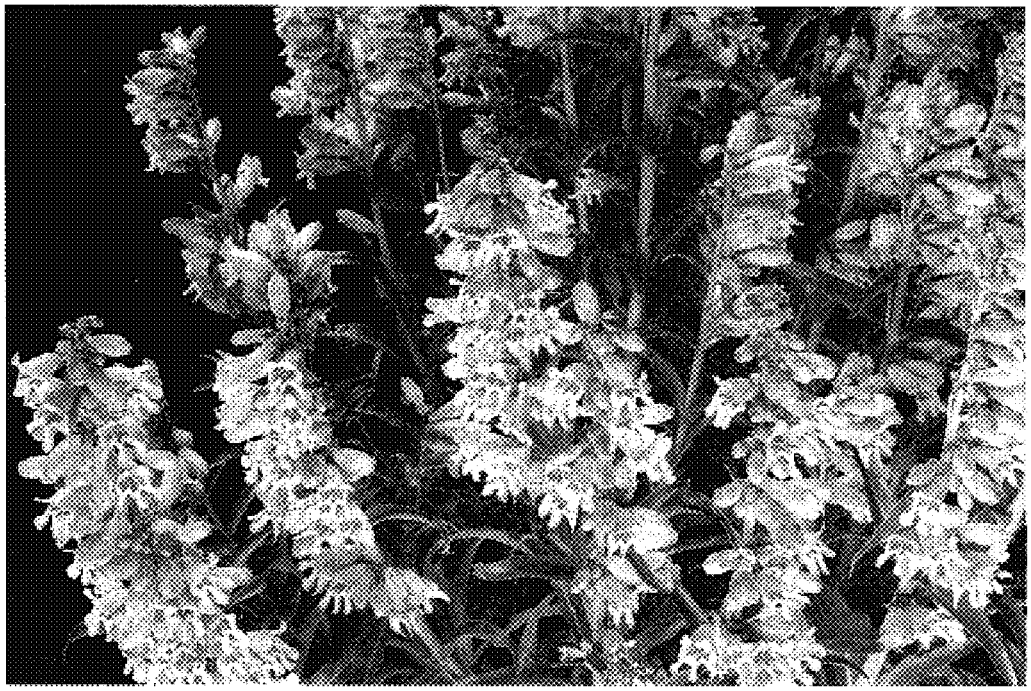

* * * * *